United States Patent [19]

Aldcroft et al.

[11] Patent Number: 5,035,879

[45] Date of Patent: Jul. 30, 1991

[54] SILICAS

[75] Inventors: Derek Aldcroft, South Wirral; John R. Newton; Peter W. Stanier, both of Cheshire, all of England

[73] Assignee: Unilever Patent Holdings BV, Rotterdam, Netherlands

[21] Appl. No.: 604,235

[22] Filed: Oct. 29, 1990

Related U.S. Application Data

[62] Division of Ser. No. 244,898, Sep. 15, 1988, Pat. No. 4,992,251.

[30] Foreign Application Priority Data

Sep. 15, 1987 [GB] United Kingdom ............... 8721644

[51] Int. Cl.$^5$ ............................................. A61K 7/16
[52] U.S. Cl. ..................................................... 424/49
[58] Field of Search ......................................... 424/49

[56] References Cited

U.S. PATENT DOCUMENTS 3,977,893  8/1976  Wason .................. 423/339
4,294,894 10/1981  Vellucci ............... 424/49
4,612,189  9/1986  Oyobe et al. .......... 424/49

FOREIGN PATENT DOCUMENTS 0139754   5/1985  European Pat. Off. .
0143848   6/1985  European Pat. Off. .
0227334   7/1987  European Pat. Off. .
0236070   9/1987  European Pat. Off. .
2446038   4/1975  France .
62-052120 3/1987  Japan .
1186706   4/1970  United Kingdom .
1264292   2/1972  United Kingdom .
1482354   8/1977  United Kingdom .
1482355   8/1977  United Kingdom .
2038303  12/1979  United Kingdom .
2146317   4/1985  United Kingdom .

Primary Examiner—Olik Chaudhuri
Assistant Examiner—Andrew Griffis
Attorney, Agent, or Firm—Cushman, Darby & Cushman

[57] ABSTRACT

Amorphous silicas suitable for use as abrasives in transparent toothpastes can be prepared by a precipitation route. These silicas are distinguished by having a BET surface area of 420 to 550 m$^2$/g, a weight mean particle size of 5 to 20 micron, a perspex abrasion value of 15 to 28, a mean pore diameter from 3 to 8 nm and a transmission of at least 70% in the R1 range from 1.444 to 1.460.

9 Claims, No Drawings

SILICAS

This is a division of application Ser. No. 07/244,898, filed Sept. 15, 1988, now U.S. Pat. No. 4,992,251.

FIELD OF THE INVENTION

This invention relates to synthetic amorphous silicas, especially precipitated silicas, of use, for example, as abrasive agents in transparent toothpaste compositions

BACKGROUND OF THE INVENTION

Toothpaste compositions are well characterized in the literature and many compositions are disclosed in patent specifications and other literature. Toothpaste compositions contain a number of specific components for example abrasive agents, fluoride sources, binders, preservatives, humectants, anti plaque agents, colouring agents, water, flavour and other optional ingredients. Of these components the abrasive agent is required to provide the appropriate cleaning and plaque removal without subjecting the tooth itself to excessive abrasion. Typically a toothpaste composition will contain from about 5% to about 50% preferably up to about 30% by weight of abrasive. Commonly used abrasives are aluminas, calcium carbonates and calcium phosphates. More recently synthetic silicas have been adopted because of their efficient cleaning, compatibility with other ingredients and their physical properties. An important property of a silica for use in transparent toothpaste formulations is refractive index, and it has been shown that this property can be controlled by careful selection of process conditions in the preparation of the silica.

PRIOR LITERATURE

Prior art silicas used as toothpaste abrasives in transparent toothpaste formulations as disclosed in GB 1,264,292 (Unilever) can be defined as either microporous gel with a surface area of 600 to 800 m$^2$/g and a pore volume of about 0.4 cm$^3$/g (low structure) or macroporous silica gel with a surface area of 250 to 350 m$^2$/g and pore volume of about 1.0 cm$^3$/g (high structure). According to Kirk-Othmer (Third Edition Vol 20, page 773) these different structured silica gels can be obtained by washing silica hydrogel at different pH values and temperatures, and in consequence a continuous range of intermediate gel structures can also be produced. For this family of silica gel structures as the surface area reduces the pore volume rises and the mean diameter of the pore system present also increases.

GB 2,038,303 (Grace) describes a family of silica gels in which the pore diameter remains essentially constant during the washing sequence. In this series of silica gels the surface area and pore volume increase together within the defined limits; surface area up to 600 m$^2$/g and a pore volume of 0.05 to 0.5 cm$^3$/g. The silica gels can be considered to be the precursor of the microporous silica gel defined in GB 1,264,292 and as such have relatively low pore volume (low structure) and give rise to high abrasivity.

Further examples of silicas useful as toothpaste abrasives with low to medium structure can be found in GB 1,482,354 & GB 1,482,355 (Huber) EPA 227,334 & EPA 236,070 (Unilever), EPA 143,848 & EPA 139,754 (Taki). GB 1,482,354 and GB 1,482,355 disclose silicas with surface areas less than 200 m$^2$/g for use in toothpastes in general, whereas EPA 227,334 and EPA 236,070 state the silicas as defined are not suitable for formulating into transparent toothpaste compositions. EPA 143,848 and EPA 139,754 define silicas by texture, refractive index and the phase after firing at 1100° C. being amorphous to X-rays, that can be used in transparent toothpastes.

GENERAL DESCRIPTION OF THE INVENTION

The amorphous silicas, especially precipitated silicas, of the invention provide a novel range of properties, combining high levels of abrasivity with good transparency when incorporated into a dentifrice formulation. The levels of abrasivity obtained with the silicas of the invention are unusually high in view of the high degree of openness of structure the silicas possess as defined by oil absorption and porosity measurements. In particular, such high levels of abrasivity coupled with good dentifrice transparency have not been obtained previously with precipitated silicas.

The silicas of the invention are capable of providing high levels of abrasion even at relatively low particle sizes i.e 5 to 10 micron range. Abrasive materials can also be obtained at particle sizes beyond the stated upper limit but they are not suitable for use in toothpastes because of the unacceptable mouth feel of the coarser particles.

In general, characterization of the pore structure of silicas containing higher levels of openness and wider pores by nitrogen adsorption techniques is not meaningful because this technique is useful only for pores up to about 60 nm diameter. To measure the full range of porosity present in such materials it is necessary to employ alternative procedures, for example oil absorption or mercury porosimetry. Since the products of this invention have considerable pore structure in excess of 60 nm it is necessary to define them by means of such techniques.

The invention provides an amorphous silica, preferably a precipitated silica, having i) a BET surface area in the range from about 420, preferably from about 430, to about 550 m$^2$/g, ii) a weight mean particle size in the range 5 microns to 20 microns, preferably below 15 microns, iii) a perspex abrasion value in the range from about 15 to about 28 preferably up to about 25, iv) a mean pore diameter in the range from about 3 to about 8nm, and v) a transmission of at least about 70% in the refractive index range of 1.444 to 1.460.

After firing at 1100° C. the silicas of the invention had a crystal structure of alpha cristobalite.

These perspex abrasion values correspond to Radioactive Dentine Abrasion values of 90 (PAV 15) to 235 (PAV 28) and 200 (PAV 25).

Usually the moisture content of the silica will be below 25% w/w preferably below 15% w/w.

The invention extends to a method of reacting a silicate solution and acid solution in the presence of electrolyte to provide precipitated silicas according to the invention.

The invention includes a method of preparing amorphous silicas, especially precipitated silicas, suitable for use as a toothpaste abrasive, and having
  i) a BET surface area in the range from about 420 to about 550 m$^2$/g,
  ii) a weight mean particle size in the range from about 5 to about 20 microns,
  iii) a perspex abrasion value in the range from about 15 to about 28, iv) a mean pore diameter in the range from about 3.0 to about 8.0 nm, v) a transmission of at least about 70% in the refractive index range of 1.444 to 1.460, which is produced by the reaction of sodium silicate, having a silica:$Na_2O$ ratio in the range from 3.2 to 3.4:1, with mineral acid, with the concentration and volume of the reactants controlled to give a reaction in the pH range from about 10 to about 10.5, in the presence of a water soluble electrolyte comprising a cation selected from sodium and potassium with an associated anion selected from chloride and sulphate wherein the electrolyte:silica weight ratio is from about 0.4 to 1 to about 1.2 to 1, the precipitation reaction being performed in the temperature range of about 45° C. to about 55° C., the pH of the reaction medium then being made acidic by addition of a mineral acid, separating and washing the resultant silica product.

Optionally the reaction medium is subjected to a hydrothermal aging step during the final acid addition step to provide materials with lower surface areas within the defined limits of the products of the invention.

A transparent toothpaste composition of the invention will contain from about 5% to about 50% by weight, preferably up to about 30%, of an amorphous, preferably precipitated, silica of the invention.

Standard Procedures

The silicas of the invention are defined in terms of their physical and chemical properties. The standard test methods used for these properties are:

i) Surface Area:

Surface area is determined using standard nitrogen adsorption methods of Brunauer, Emmett and Teller (BET), using a single point method with a Sorpty 1750 apparatus supplied by Carlo Erba company of Italy. The sample was outgassed under vacuum at 270° C. for 1 hour before measurement.

ii) Oil Absorption:

The oil absorption is determined by the ASTM spatula rub-out method (American Society of Test Material Standards D, 281).

The test is based upon the principle of mixing linseed oil with a silica by rubbing with a spatula on a smooth surface until a stiff putty-like paste is formed which will not break or separate when it is cut with the spatula. The volume of oil used is then put into the following equation:

$$\text{Oil absorption} = \frac{cm^3 \text{ oil absorption} \times 100}{\text{wt. of silica sample in gms}}$$

$$= cm^3 \text{ oil}/100 \text{ g silica}$$

iii) Weight Mean Particle Size:

The weight mean particle size of the silicas was determined with the aid of a Malvern Particlesizer, Model 3600 E. This instrument, made by Malvern Instruments, Malvern, Worcestershire uses the principle of Fraunhoffer diffraction utilizing a low power He/Ne laser. Before measurement the sample was dispersed ultrasonically in water for a period of 7 minutes to form an aqueous suspension.

iv) Perspex Abrasion Value:

This test is based upon a toothbrush head brushing a perspex plate in contact with a suspension of the silica in a sorbitol/glycerol mixture. Normally the slurry composition is as follows:

| | |
|---|---|
| Silica | 2.5 grams |
| Glycerol | 10.0 grams |
| Sorbitol Syrup* | 23.0 grams |

*Syrup contains 70% sorbitol/30% water.

All components are weighed into a beaker and dispersed for 2 minutes at 1500 rpm using a simple stirrer. A 110 mm×55 mm×3 mm sheet of standard clear Perspex is used for the test, supplied by Imperial Chemical Industries Plc under code 000.

The test is carried out using a modified Wet Paint Scrub Tester produced by Research Equipment Limited, Wellington Road, Hampton Hill, Middlesex. The modification is to change the holder so that a toothbrush can be used instead of a paint brush. In addition a weight of 14 ozs is attached to the brush to force the brush onto the perspex plate.

A Galvanometer is calibrated using a 45° Plaspec gloss head detector and a standard (50% gloss) reflecting plate. The Galvanometer reading is adjusted to a value of 50 under these conditions. The reading of the fresh perspex plate is then carried out using the same reflectance arrangement.

The fresh piece of perspex is then fitted into a holder. Two mls of the dispersed silica, sufficient to lubricate fully the brushing stroke, is placed on the plate and the brush head lowered onto the plate. The machine is switched on and the plate subjected to three hundred strokes of the weighted brush head. The plate is removed from the holder and all the suspension is washed off. It is then dried and re-measured for its gloss value. The abrasion value is the difference between the unabraded value and the value after abrasion.

This test procedure, when applied to known abrasives, gave the following values:

| | Perspex abrasion value |
|---|---|
| Calcium carbonate (15 micron) | 32 |
| Silica xerogel (10 micron) prepared by UK 1264292 method | 25 |
| Alumina trihydrate (Gibbsite) (15 micron) | 16 |
| Calcium pyrophosphate (10 micron) | 14 |
| Dicalcium phosphate dihydrate (15 micron) | 7 | v) Loose Bulk Density:

Loose bulk density is determined by weighing approximately 180 ml of silica into a dry 250 ml measuring cylinder, inverting the cylinder ten times to remove air pockets and reading the final settled volume.

$$\text{Loose bulk density} = \frac{\text{Weight}}{\text{Volume}} \times 1000 \text{ g/l}$$

vi) Electrolyte Levels:

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

vii) Moisture Loss at 105° C.:

Moisture loss is determined by the loss in weight of a silica when dried to constant weight in an electric oven at 105° C.

viii) Ignition Loss at 1000° C.:

Ignition loss is determined by the loss in weight of a silica when ignited in a furnace at 1000° C. to constant weight.

ix) pH:

This measurement is carried out on a 5% w/w suspension of the silica in boiled demineralised water ($CO_2$ free).

x) Crystal Form After Firing at 1100° C.:

A sample of the silica is fired in an electric muffle furnace for one hour at 1100° C. The treated sample is allowed to cool and the crystal structure present identified from the trace obtained from an x-ray diffractometer.

xi) Mercury intrusion volume:

Mercury intrusion volumes are determined (in cc/g) by standard mercury intrusion procedures using a Micromeritics Autopore 9220 mercury porosimeter. The pore radius is calculated from the Washburn equation using values of surface tension for mercury of 485 dynes/cm and contact angle of 140°.

Prior to measurement the sample was outgassed at room temperature to a pressure of 50 microns of mercury. The mercury intrusion volume recorded is that occurring over the range of calculated pore diameters of 0.05 to 1.0 micron.

xii) Refractive index (RI)/transmission:

The sample of silica is dispersed in a range of Sorbitol syrup (70% Sorbitol)/water mixtures. After de-aeration, usually 1 hour, the transmission of the dispersions is determined using a spectrophotometer at 589 nm; water being used as blank. The refractive index of each dispersion is also measured using an Abbe refractometer.

A graphical representation of transmission plotted against refractive index allows the range of refractive indices over which the transmission exceeds 70% to be determined. The maximum transmission of the sample and the refractive index at which this is obtained can also be estimated from this graph.

xiii) Mean pore diameter (MPD):

This parameter is related to the surface area and pore volume and, using a cylindrical pore model, is calculated for a silica product with the formula:

$$MPD\ (nm) = \frac{\text{pore volume } (ccg^{-1}) \times 4000}{\text{surface area } (m^2g^{-1})}$$

Pore volume is the mercury intrusion volume defined in (xi).

xiv) Radioactive Dentine Abrasion Test (RDA):

The procedure follows the method for assessment of dentifrice abrasivity recommended by the American Dental Association (Journal of Dental Research 55 (4) 563, 1976). In this procedure extracted human teeth are irradiated with a neutron flux and subjected to a standard brushing regime. The radioactive phosphorus 32 removed from the dentin in the roots is used as the index of the abrasion of the dentifrice tested. A reference slurry containing 10 g of calcium pyrophosphate in 15 ml of 0.5% aqueous solution of sodium carboxymethyl cellulose is also measured and the RDA of this mixture is arbitrarily taken as 100. The precipitated silica to be tested is prepared as a suspension at the same concentration as the pyrophosphate and submitted to the same brushing regime.

By examining a range of silicas, including those described in the present invention, it has been found there is a correlation between plastics abrasion value and RDA over fifteen samples with a correlation coefficient of 0.91 (confidence 99%).

SPECIFIC DESCRIPTION OF THE INVENTION

Examples of the preparation of precipitated silicas will now be given to illustrate but not limit the invention. Example 7 is included as a comparison to show the criticality of the reaction temperature on the transmission and pore diameter of the resulting silica. Example 6 demonstrates the criticality of the aging period.

A heated stirred reaction vessel was used for the silicate/acid reaction.

The solutions used in the process were as follows:
i) Sodium silicate solutions having a $SiO_2:Na_2O$ ratio in the range of 3.2 to 3.4:1.
ii) A sulphuric acid solution of specific gravity 1.11 (16.1% W/W solution) to 1.15 (21.4% W/W solution).
iii) An electrolyte solution as defined in each example.

The following procedure was adopted in the preparation of the precipitated silicas of the invention. Values of reactant concentrations and volumes, and reaction temperatures are given in Table 1.

(A) liters of water were placed in the vessel together with (B) liters of electrolyte solution and (C) liters of the sodium silicate solution. This mixture was then stirred and heated to (E) ° C.

The sodium silicate ((D) liters) and sulphuric acid ((F) liters) solutions were then added simultaneously over a period of about 20 minutes with stirring while maintaining the temperature at (E) ° C. The flow rates of the silicate and acid solutions were uniform throughout the addition period to ensure that a constant pH from about 10 to about 10.5 was maintained in the vessel. Sulphuric acid solution was then added over a period of 10 minutes with continued mixing to reduce the pH of the slurry to the range of 3.0 to 4.0. During this addition of acid the temperature was maintained. Optionally a hydrothermal aging step can be introduced during this final acid addition step if materials with lower surface areas are required. The resultant slurry was then filtered and washed with water to remove excess electrolyte. Typically, for a toothpaste application, the residual electrolyte would be less than 2% on a dry weight basis. After washing, the filter cake in each example was dried and comminuted to the desired particle size range. Alternatively the filter cake can be hot air milled to the desired particle size range.

The effect of aging the reactants slurry on the properties of the derived dried product is illustrated by examples 5, 6, 9 and 11. Examples 6 and 9 demonstrate how the length of the aging period is critical to the key properties of the silicas of the invention. Aging for too long lowers the surface area of the resultant silica below the specified limit giving rise to a silica which does not fulfil the requirement for transparency when formulated into a dentifrice composition. The rate of reduction in surface area is dependant upon the electrolyte type and concentration as shown by examples 6, 9 and 11.

The precipitated silicas obtained had the properties, expressed on a dry weight basis listed in Table II.

The amorphous silicas prepared as described provided satisfactory cleaning properties in the transparent toothpastes in which they were incorporated, using the formulations described in GB 1186706. Typical formulations using the silicas of the invention at different levels of incorporation, i.e. 6% w/w, 14% w/w 20% w/w and 30% w/w, are given in Table III. These toothpaste compositions had commercially suitable properties with respect to stability and usage.

TABLE I

| EXAMPLE NO. | 1 | 2 | 3 | 4 | 5* | 6= |
|---|---|---|---|---|---|---|
| VESSEL CAPACITY (LITERS) | 64 | 325 | 325 | 325 | 64 | 64 |
| WATER VOLUME (A) (LITERS) | 14.4 | 109.0 | 109.0 | 101.0 | 15.1 | 15.1 |
| ELECTROLYTE USED | NaCl | NaCl | NaCl | NaCl | NaCl | NaCl |
| CONCN. OF ELECTROLYTE (% W/W) | 25 | 25 | 25 | 25 | 25 | 25 |
| VOL OF ELECTROLYTE (B) (LITERS) | 6.67 | 34.7 | 34.7 | 34.7 | 6.67 | 6.67 |
| SILICATE RATIO $SiO_2/Na_2O$ BY WEIGHT | 3.32 | 3.34 | 3.34 | 3.34 | 3.27 | 3.27 |
| $SiO_2$ CONCN. IN SODIUM SILICATE (% W/W) | 16.63 | 17.0 | 17.0 | 16.23 | 16.81 | 16.81 |
| SILICATE VOL. (C) (LITERS) | 0.2 | 1.0 | 1.0 | 1.0 | 0.2 | 0.2 |
| SILICATE VOL. (D) (LITERS) | 19.8 | 100.3 | 100.3 | 106.0 | 19.6 | 19.8 |
| ACID CONCN. (% W/W) | 18.5 | 18.2 | 18.2 | 17.8 | 19.3 | 19.3 |
| ACID VOL. (LITERS) (F) | 7.5 | 39 | 39 | 41.9 | 7.2 | 7.2 |
| TEMPERATURE (E) (°C.) | 48 | 52 | 52 | 55 | 50 | 50 |

| EXAMPLE NO. | 7 | 8 | *9 | 10 | *11 |
|---|---|---|---|---|---|
| VESSEL CAPACITY (LITERS) | 64 | 64 | 64 | 64 | 64 |
| WATER VOLUME (A) (LITERS) | 13.9 | 15.7 | 15.4 | Nil | Nil |
| ELECTROLYTE USED | NaCl | KCl | KCl | $Na_2SO_4$ | $Na_2SO_4$ |
| CONCN. OF ELECTROLYTE (% W/W) | 25 | 20 | 20 | 20 | 20 |
| VOL OF ELECTROLYTE (B) (LITERS) | 6.67 | 7.06 | 7.06 | 20.15 | 20.15 |
| SILICATE RATIO $SiO_2/Na_2O$ BY WEIGHT | 3.29 | 3.23 | 3.23 | 3.23 | 3.23 |
| $SiO_2$ CONCN. IN SODIUM SILICATE (% W/W) | 16.35 | 17.09 | 17.09 | 17.09 | 17.09 |
| SILICATE VOL. (C) (LITERS) | 0.2 | 0.2 | 0.2 | 0.2 | 0.2 |
| SILICATE VOL. (D) (LITERS) | 20.2 | 19.16 | 19.16 | 19.16 | 19.16 |
| ACID CONCN. (% W/W) | 18.1 | 19 | 18.4 | 18.4 | 18.9 |
| ACID VOL. (LITERS) (F) | 7.7 | 6.92 | 7.28 | 7.28 | 7.1 |
| TEMPERATURE (E) (°C.) | 60 | 50 | 50 | 55 | 55 |

*EX 5 HYDROTHERMALLY AGED @ pH 8 FOR 80 MINS.
=EX 6 HYDROTHERMALLY AGED @ pH 8 FOR 360 MINS.
*EX 9 & 11 HYDROTHERMALLY AGED @ pH 8 FOR 75 MINS.

TABLE II

| EXAMPLE NO. | 1 | 2 | 3 | 4 | 5 | 6 |
|---|---|---|---|---|---|---|
| TEST | | | | | | |
| SURFACE AREA ($M^2g^{-1}$) | 531 | 505 | 505 | 515 | 432 | 418 |
| MEAN PORE DIAMETER (NM) | 3.0 | 5.0 | 7.2 | 3.9 | 3.8 | 3.8 |
| PERSPEX ABRASION VALUE | 17 | 22 | 19 | 20 | 25 | 22 |
| MAX % TRANSMISSION | 96.5 | 71.5 | 71.5 | 79.5 | 96.0 | 38.3 |
| @ REFRACTIVE INDEX | 1.451 | 1.451 | 1.451 | 1.4505 | 1.452 | 1.432 |
| FORM AFTER FIRING @ 1100° C.* | Ac | Ac | Ac | Ac | Ac | Ac |
| MERCURY INTRUSION VOL. (cc $g^{-1}$) | 0.40 | 0.63 | 0.91 | 0.50 | 0.41 | 0.40 |
| IGNITION LOSS @ 1000° C. (%) | 10.2 | 9.2 | 9.2 | 9.5 | 9.8 | 9.4 |
| MOISTURE LOSS @ 105° C. (%) | 4.5 | 3.8 | 3.8 | 3.9 | 4.7 | 4.3 |
| WEIGHT MEAN PARTICLE SIZE (MICRON) | 18.0 | 10.6 | 5.5 | 8.9 | 15.0 | 10.0 |
| pH | 5.8 | 6.9 | 6.9 | 6.7 | 6.0 | 6.0 |
| ELECTROLYTE LEVEL $SO_4=$ (%) | 0.18 | 0.05 | 0.05 | 0.08 | 0.10 | 0.17 |
| ELECTROLYTE LEVEL $CL-$ (%) | 0.18 | 0.10 | 0.10 | 0.10 | 0.12 | 0.20 |
| OIL ABSORPTION (CC/100 g) | 130 | 90 | 100 | 75 | 130 | 100 |

| EXAMPLE NO. | 7 | 8 | 9 | 10 | 11 |
|---|---|---|---|---|---|
| TEST | | | | | |
| SURFACE AREA ($M^2g^{-1}$) | 465 | 483 | 415 | 479 | 450 |
| MEAN PORE DIAMETER (NM) | 2.2 | 3.7 | 4.2 | 5.2 | 4.8 |
| PERSPEX ABRASION VALUE | 19 | 23 | 25 | 17 | 19 |
| MAX % TRANSMISSION | 53.5 | 96 | 55 | 84.5 | 94.1 |
| @ REFRACTIVE INDEX | 1.446 | 1.458 | 1.4426 | 1.4581 | 1.45 |
| FORM AFTER FIRING @ 1100° C.* | Ac | Ac | Ac | Ac | Ac |
| MERCURY INTRUSION VOL. (cc $g^{-1}$) | 0.26 | .45 | .43 | .63 | .55 |
| IGNITION LOSS @ 1000° C. (%) | 11.6 | 8.5 | 8.6 | 8.8 | 10 |
| MOISTURE LOSS @ 105° C. (%) | 5.8 | 1.7 | 2.7 | 3.8 | 7.4 |
| WEIGHT MEAN PARTICLE SIZE (MICRON) | 13.5 | 16.8 | 8.6 | 9.7 | 8.5 |
| pH | 6.3 | 6.4 | 6.5 | 6.5 | 6.4 |
| ELECTROLYTE LEVEL $SO_4=$ (%) | 0.07 | .05 | .04 | .05 | .06 |
| ELECTROLYTE LEVEL $CL-$ (%) | 0.08 | .09 | .09 | .01 | .02 |
| OIL ABSORPTION (CC/100 g) | 121 | 105 | 100 | 120 | 115 |

*Ac indicates alpha cristobalite

TABLE III

EXAMPLES OF THE INVENTION IN TYPICAL TRANSPARENT DENTIFRICE FORMULATIONS

| FORMULATION | 1 | 2 | 3 | 4 |
|---|---|---|---|---|
| Sorbosil TC10* | 10.0 | 8.0 | 5.4 | 3.0 |
| Silica of invention | 6.0 | 14.0 | 20.0 | 30.0 |
| Sodium CMC | 0.5 | 0.6 | 0.5 | 0.5 |
| Sorbitol, 70% non-crystallisable | 60.0 | 68.0 | 52.1 | 54.8 |
| Polyethylene glycol 1500 | 3.0 | Nil | 3.0 | 5.0 |
| Sodium Lauryl Sulphate | 1.5 | 1.5 | 1.5 | 1.5 |
| Glycerine | 12.0 | 6.0 | 11.6 | Nil |
| Sodium Monofluro-phosphate | 0.8 | Nil | 0.8 | 0.8 |
| Flavour | 1.0 | 1.0 | 1.1 | 1.1 |
| Saccharin | 0.2 | 0.2 | 0.2 | 0.2 |
| Water and Minor Ingredients | to 100 | to 100 | to 100 | to 100 |
| Properties | | | | |
| Initial density @ 25° C. g.ml$^{-1}$ | 1.32 | 1.33 | NM | NM |
| RDA | 60 | 120 | 130 | NM |

NM - not measured
*Sorbosil TC10 is a thickening silica obtainable from Crosfield Chemicals of Warrington, England.

We claim:

1. A toothpaste composition containing from about 5% to about 50% by weight of an amorphous silica having
    i) a BET surface area in the range from about 420 to about 550 m$^2$/g,
    ii) a weight mean particle size in the range from about 5 to about 20 microns,
    iii) a perspex abrasion value in the range from about 15 to about 28,
    iv) a mean pore diameter in the range from about 3.0 to about 8.0 nm,
    v) a transmission of at least about 70% in the refractive index range of 1.444 to 1.460, and
    vi) an oil absorption in the range from about 70 to about 140 cc/100 g.

2. A toothpaste composition according to claim 1 characterized in that the amorphous silica is a precipitated silica.

3. A toothpaste composition according to claim 1 wherein the phase of the amorphous silica after firing at 1100° C. is alpha-cristobalite.

4. A toothpaste composition according to claim 1 containing up to 30% by weight of the amorphous silica.

5. A toothpaste composition according to claim 1 wherein the surface area of the amorphous silica is at least about 430 m$^2$/g.

6. A toothpaste composition according to claim 1 wherein the amorphous silica has a moisture content of less than about 25% w/w.

7. A toothpaste composition according to claim 6 wherein the amorphous silica has a moisture content less than about 15% w/w.

8. A toothpaste composition according to claim 1 wherein the amorphous silica has a weight mean particle size of not more than about 15 microns.

9. A toothpaste composition according to claim 1 wherein the amorphous silica has a perspex abrasion value up to about 25.

* * * * *